(12) United States Patent
Müller et al.

(10) Patent No.: US 6,689,591 B2
(45) Date of Patent: Feb. 10, 2004

(54) METHOD OF REDUCING KETO-CARBOXYLIC ACIDS AND THEIR ESTERS

(75) Inventors: Michael Müller, Jülich (DE); Michael Wolberg, Jülich (DE); Werner Hummel, Titz (DE); Christian Wandrey, Jülich (DE)

(73) Assignee: Forschungszentrum Jülich GmbH, Jülich (DE)

( * ) Notice: Subject to any disclaimer, the term of this patent is extended or adjusted under 35 U.S.C. 154(b) by 84 days.

(21) Appl. No.: 10/041,968

(22) Filed: Jan. 7, 2002

(65) Prior Publication Data
US 2002/0098557 A1 Jul. 25, 2002

Related U.S. Application Data

(63) Continuation-in-part of application No. PCT/EP00/06287, filed on Jul. 5, 2000.

(30) Foreign Application Priority Data

Jul. 9, 1999 (DE) .......................... 199 32 038
Aug. 11, 1999 (DE) .......................... 199 37 825

(51) Int. Cl.$^7$ .................................................. C12P 7/46
(52) U.S. Cl. ....................................................... 435/146
(58) Field of Search ........................................ 435/146

(56) References Cited

U.S. PATENT DOCUMENTS 5,342,767 A    8/1994  Wong et al.
6,037,158 A  * 3/2000  Hummel et al.

FOREIGN PATENT DOCUMENTS

| EP | 0 569 998 | 11/1993 |
| WO | WO 97/00968 | 1/1997 |
| WO | 99/47684 | 9/1999 |
| WO | WO 00/36134 | 6/2000 |

OTHER PUBLICATIONS

Patel R.N. et al. "Enantioselective Microbial Reduction of 3,5–Dioxo–6–(Benzyloxy) Hexanoic Acid, Ethyl Ester", *Enzyme and Microbial Technology*, vol. 15, No. 12, 1993 pp. 1014–1021.

Peters, J. et al. "Studies on the Distribution and Regulation of Microbial Keto Ester Reductases", *Applied Microbiology and Biotechnology*, Berlin, vol. 38, 12/92, pp. 334–340.

* cited by examiner

*Primary Examiner*—Johann Richter
*Assistant Examiner*—Paul A. Zucker
(74) *Attorney, Agent, or Firm*—Klaus J. Bach

(57) ABSTRACT

In a method of reducing diketocarboxylic acids or hydroxyketocarboxylic acids or their esters, at least one keto group is converted to a hydroxyl group in the presence of lactobacillus species.

10 Claims, No Drawings

METHOD OF REDUCING KETO-CARBOXYLIC ACIDS AND THEIR ESTERS

This is a Continuation-In-Part application of international application PCT/EP00/06287 filed Jul. 05, 2000 and claiming the priority of German applications 199 32 038.1 filed Jul. 09, 1999 and 199 37 825.8 filed Aug. 11, 1999.

BACKGROUND OF THE INVENTION

The present invention relates to a method of reducing diketocarboxylic acids or hydroxyketo carboxylic acids or their esters to form hydroxyl compounds.

Optically active hydroxyl compounds are valuable chiral materials. Chiral diols are, for example, important raw materials for a multitude of active compounds in the pharmacy and in plant protection and also for catalysts.

For the manufacture of chiral compounds biotechnological processes can be used which utilize either whole microorganism cells or isolated enzymes.

Suitable enzymes for the synthesis of alcohols are, among others, oxidoreductases, which are described in EP 911 07 067.0 (produced from *lactobacillus kefir*), EP 0 796 691 A2 and PCT/DE99/00848 (from *lactobacillus brevis*). However, the syntheses require accessibility to the suitable enzymes, the addition of a soluble coenzyme (NADH, NADPH) and a coenzyme regeneration system. Likewise, in WO97/00968 the use of reductases for the reduction of keto groups is described.

In addition U.S. Pat. No 5,342,767 discloses a process, wherein a reduction is performed with the use of alcohol dehydrogenases from lactobacillus kefir.

DE 196 10 984.1 also discloses a method wherein an alcohol dehydrogenase is utilized. In addition to the purified enzymes also whole cells can also be utilized. The subject of this invention, however, does not relate to the reaction of compounds with two or more keto groups. The process is, furthermore, not concerned with the conversion of keto carboxylic acids and their esters.

Microorganisms present a cost-effective alternative to enzymes for reduction processes. However, these processes have often a low yield (F. Aragazzini et al., Appl. Microbiol. Biotechnol. (1986) 24, 175–177). Furthermore, yield-lowering side reactions often occur and the products do not always have a sufficient enantiomeric purity. The production yield and quality depend greatly on the strain used and on the growth conditions.

From the European patent application 0 569 998 A2 finally a method is known wherein various microorganisms are used for the reduction of diketoesters containing ether groups. The microorganisms usable herein include a large number of yeasts and bacteria, but no lactobacillus species.

It is accordingly the object of the present invention to provide a method for the reduction of diketo- or hydroxy-lketocarboxylic acids or the esters thereof, which does not have the disadvantages pointed out above. Under hydroxyl groups also hydroxyl groups are to be understood which are masked by protective groups.

SUMMARY OF THE INVENTION

In a method of reducing diketocarboxylic acids or hydroxyketocarboxylic acids or their esters, at least one keto group is converted to a hydroxyl group in the presence of lactobacillus species.

In a preferred embodiment, the reduction is performed so as to provide diols.

The method according to the invention includes in particular the catalytic reduction of the prochiral 3.5-dioxocarboxylic acid derivatives according to the formula 1:

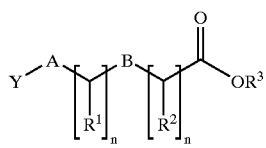

Formula 1

A, B=C=O, CHOΣ, with Σ=H or a protective group for the hydroxyl function; wherein A and B may be identical or different.

$R^1, R^2$=H or a component of the group consisting of alkyl, alkenyl, alkynyl, cycloalkyl, cycloalkenyl, aryl, aralkyl, cycloalkylalkyl, wherein the components may also be mono- or polysubstituted by heteroatoms, such as Si, N, P, O, S, F, Cl, Br, or I or they may be completely replaced by heteroatoms.

$R^3$=H, metal cations or a component of the group alkyl, alkenyl, alkynyl, cycloalkyl, cycloalkenyl, aryl, aralkyl, cycloalkylalkyl, wherein the components may be mono or polysubstituted by hetero atoms, such as, for example, Si, N, P, O, S, F, Cl, Br, or I.

Y=a component of the group comprising alkyl, alkenyl, alkynyl, cycloalkyl, cycloalkenyl, aryl, aralkyl, cycloalkylalkyl, wherein the components may be mono- or polysubstituted by heteroatoms such as, for example, Si, N, P, O, S, F, Cl, Br, or I. Excluded is X—$CH_2$—O—$CH_2$— wherein X=alkyl, cycloalkyl, aryl, aralkyl, cycloalkylalkyl. Among the halogens, fluorine and chlorine are particularly preferred. n=0–10.

Alkyls are considered to be straight-chain as well as branched saturated carbon chains. Methyl, ethyl, n-propyl, i-propyl, t-butyl, pentyl, i-pentyl, n-hexyl, i-hexyl, may be mentioned as examples.

Alkynyl comprises straight-chain and branched unsaturated hydrocarbons, which contain at least one —C≡C— band such as for example ethynyl or propynyl.

Cycloalkyl comprises saturated annular hydrocarbon chains which consist of three, four, five, six or seven hydrocarbon atoms.

Cycloalkenyl designates annular hydrocarbons with five, six, seven or eight carbon atoms.

Aryl comprises aromatic systems including heteroaromats and subsituted aromatic systems such as for example phenyl, p-methylphenyl or furanyl.

Aralkyl are aryl rests which are bound by way of alkyl groups, for example benzyl rests.

Cycloalkylalkyl comprises cycloalkyl radicals which are bonded by way of alkyl groups.

Also, reactions of the compounds according to formulas 2, 3, and 4 are possible.

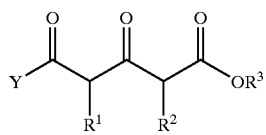

Formula 2

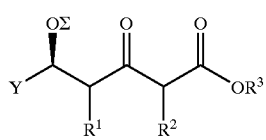

Formula 3

-continued

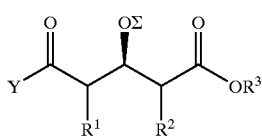

Formula 4

Herein, $R^1$, $R^2$, $R^3$ and Y have the same meaning as in formula 1.
$\Sigma$=H or protective groups for the hydroxyl functions.
With the method according to the invention, it is therefore possible to produce 3,5 dihydrocarboxylic acid derivatives as represented by the following formula 5.

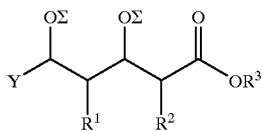

Formula 5

Herein $R^1$, $R^2$, $R^3$ and Y have the same meaning as in formula 1.
$\Sigma$=H or protective groups for the hydroxyl function.
In contrast to the state of the art, with the method according to the invention compounds according to the formulas 3 and 4 can be converted as substrates.
Depending on the configurations at the stereocenters C-3 and C-5, the 3,5-dihydroxycarboxylic acid derivatives of the formula 5 prepared in accordance with the invention can be utilized in a controlled manner during the synthesis of chiral natural substances, pharmaceutical and agricultural active compounds, catalysts and inhibitors. Examples, herefor are HMG-CoA reductase inhibitors of the mevinic acid type and the lipase-inhibitors of the lipstatin-type.
Other natural substances or effective compounds require other configurations of the stereogenic centers in position C-3 and C-5. This is also possible with the present invention.
The method according to the invention facilitates, during the reduction of 3,5-dioxocarboxylic acid derivatives, the area selective introduction of a hydroxyl group in position C-3 or C-5 or C-3 and C-5, wherein a product with a r-configuration is obtained.
Concerning the designation r-configuration, the following is pointed out as an example with respect to formula 3:
In the formula 3, the O$\Sigma$-group in the 5-position projects from the paper plane whereas Y and the carbon atoms of the basic carbon structure are disposed in the plane of the paper:

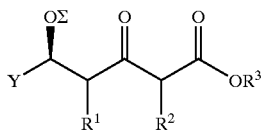

Formula 3

This configuration will be designated below as the r-configuration independently of Y.
Furthermore, the method according to the invention facilitates during the reduction of 3,5 dioxycarboxylic acid derivatives of the formula 2, a specific fixing of the stereo centers in the positions C-2 and C-4. This is particularly true for a case in which R1 and R2 differ from H, and R1 represents for example a methyl group. The enantiomeric purity as well as the diastereomeric purity are very high in that case (>95%).
In accordance with the invention also mixtures can be produced with the reduction method, which include compounds with different hydroxyl group contents. Examples herefor are mixtures, which consist of compounds of the formulae 3, 4, and 5, wherein $R^1$, $R^2$=H; Y=—CH$_3$ or —CH$_2$Cl and $R^3$=C(CH$_3$)$_3$.

The method according to the invention is performed with Lactobacillus types. Basically, any Lactobacillus type may be used. Particular preference however is given to the use of *Lactobacillus kefir* and *Lactobacillus brevis*.

The method according to the invention can be performed under customary fermentation conditions and in the customary reactors.

As co-substrate, a carbon-containing substrate, which can easily be metabolized, such as glucose, may be used. In this way, the reduction equivalents, which are consumed during the conversion, can be replaced.

The reactions are performed in accordance with the invention at temperatures of 10 to 50° C., preferably at 15–40° C.

The pH value is between 2 and 10, preferably between 4 and 8. To ensure a suitable pH value, any buffer substance common in fermentation tchnology may be used. These are for example triethanolamine, phosphate buffers, phosphate-citrate-buffers, 2-amino-2-(hydroxymethyl)-1,3-propandiol-buffers, 2[N-morpholino] ethanesulfonic acid buffers (MES) or tris buffers. The concentration ranges for the buffers are preferably between 50 and 500 mmol/l.

As reactors any known reactor type may be used. For example, conventional stirred reactors as well as fixed bed reactors can be employed.

With the method according to the invention, racemate separations or diastereomer separations, which are costly and may detrimentally affect the environment'can be omitted. The binding and cleavage of a stoichiometric amount of a homochiral auxiliary group which is required in a diastereoselective synthesis, is avoided. Furthermore, the carbon structure of the dihydroxycarboxylic acid esters is complete already in the initial compounds that is, the stereocenters are introduced into the overall synthesis sequence only at a later point in time. In this way, the loss of homochiral material is kept low. At the same time, very high stereo selectivities are achieved with the method according to the invention. With the use of whole cells, there is also no need to introduce expensive coenzyme and coenzyme regeneration systems into the reaction.

The compounds according to formulas 1 to 5 made in accordance with the invention can be used particularly for the production of chiral natural substances, pharmaceutical and agricultural active compounds, catalysts and inhibitors. Examples herefor are HMG-CoA reductase inhibitors of the mervinic acid type and lipase-inhibitors of the lipstatin type.

Below, the invention will be described in greater detail on the basis of examples.

EXAMPLE 1
Production of Lactobacillus Cells (*Lactobacillus Kefir*)

Cells for the reduction can be obtained by multiplying a stock culture of *Lactobacillus kefir* (for example, DSM 20587) in the following medium:

For 1 liter: 10 g casein peptone, tryptically digested; 10 g meat extract; 5 g yeast extract, 20 g glucose; 1 g Tween 80; 2 g $K_2HPO_4$; 5 g Na-acetate; 2 g diammonium citrate; 0.2 g $MgSO_4 \times 7H_2O$; 0.05 g $MnSO_4 \times H_2O$; pH=6.2–6.5.

After 24 hrs growth, the cells are harvested by centrifugation. They can be stored by freezing.

EXAMPLE 2
Whole Cell Transformation of Tert-butyl 6-chloro-3,5-dioxohexanoate (I) using *Lactobacillus kefir*.

Synthesis of the secondary alcohols (S)-II, (R)-III and (3R, 5S)-IV (formula scheme I).

The whole cell transformations described below are performed at room temperature using cells of the *Lactobacillus kefir* which are obtained as described in example 1. The diketo compound I is prepared as described in M. Wolberg, W. Hummel, M. Muller, pat. publ. DE 198 47 302.2, 1998.

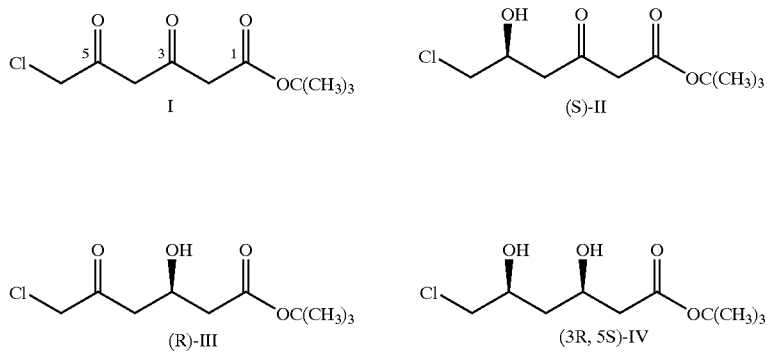

FIG. 1

Performing the Microbial Reduction

In a 50 ml beaker, 0.61 g moist cell mass is suspended in 0.5 ml phosphate-citrate buffer (250 mM, pH 5.5) by stirring. From this cell suspension 0.9 ml are provided with 1 ml glucose solution (5 M, autoclaved), 8 ml phosphate-citrate buffer (250 mM, pH 5.5) and 50 μl of tert-butyl 6-chlorine-3,5-dioxohexanoate (1). The reaction mixture is stirred with a magnetic stirrer.

Reaction Control

After 1 hour, 2 hours, 6.5 hours and 10.5 hours, samples are taken. For this purpose, 40 μl of the reaction solution are added to 200 μl ethyl acetate. After shaking, the organic phase is analyzed by gas chromatography for which a quadrupole mass spectrometer with electron impact ionization (70 eV) is used as detector (GC-MS coupling).

GC capillary column; HP-5MS (5% phenylmethylsiloxane; 30.0 m×250 μm×0.25 μm nominal).

Temperature program: 1 min 60° C., then heating to 280° C. (15° C./min)

Gas flow: 1.0 ml/min of helium.

Injection: split 50:1.

Retention Times

| I: | 8.21 min |
|---|---|
| (S)-II: | 8.10 and 8.84 min (see below) |
| (R)-III: | 9.06 min |
| (3R, 5S)-IV: | 9.26 min. |

The diketo compound I is detected as furanone, just like the hydroxyketoester (R)-III (HCl separation in the injector, see also the formula scheme IV). The hydroxyketoester (S)-II produces two signals in the GC injector by partial thermal lactone formation.

The course of the microbial reduction can be monitored by means of the chromatograms. In the first two samples, the growing proportions of the hydroxyketones S)-II and (R)-III can be detected, whereas, in the samples taken at later times the signal for the dihydroxy compounds (3R, 5S)-IV gains in intensity. Since at the same time, the signals for the hydroxyketones (S)-II and (R)-III become less intense, it can be assumed that the dehyroxy compound (3R, 5S)-IV is formed by microbial reduction of the intermediately occurring hydroxyketones (S)II and (R)-III.

Procedure

After 12.5 hours, the reaction is interrupted by centrifuging the cells. The cell pellets and the centrifuging residue are extracted separately, each twice with ethyl acetate. After drying of the combined organic phases with sodium sulfate and concentrating in a rotary evaporator, 44 mg of a raw product are obtained.

Product Analysis a) Determination of the Proportions of the Reaction Products in the Raw Product For a decomposition-free gas chromatographic analysis GC-MS), method, see above) 1.5 mg of the raw product of the microbial reduction are placed into a 1.5 ml GC-glass vial together with 0.5 ml dichloromethane and 10 μl of trifluoroactic anhydride (TFAA) and 10 μl pyridine are added. Subsequently, the glass vial is sealed with a septum and maintained in a water bath for 30 mm at 40° C.

The subsequent GC-MS-analysis shows four main signals, which can be attributed to the derivatization products (3R, 5S)-V, (S)-V1, (S)-VII, and VIII on the basis of the respective mass spectra (formula schematic 11).

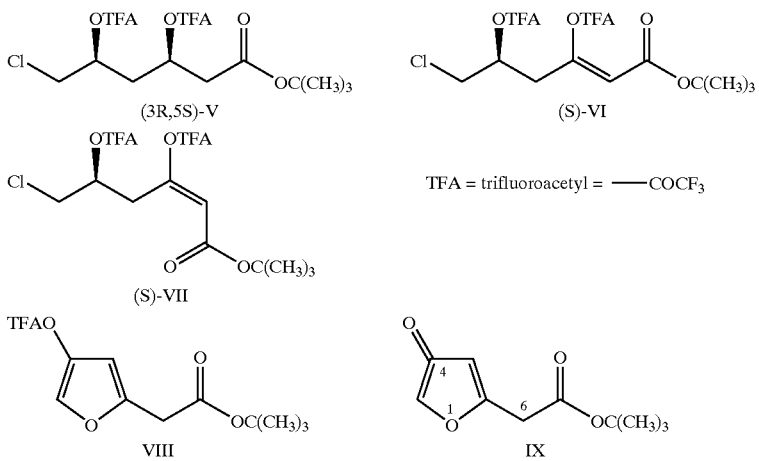

FIG. 2

The derivate (3R, 5S)-V is formed from the microbial reduction product (3R, 5S)-IV, whereas the hydroxyketone (S)-11 reacts to form the two stereoisomeric bisacylation products (S)-VI and (S)-VII. The cyclic derivative VIII is formed from the furanone IX, whose formation from the diketo compound I during the microbial reaction is known (by-product by intramolecular alkylation, see M. Wolberg, W. Hummel, M. Müller, DE 198 57 302). A derivative of the hdyroxyketoester (R)-III cannot be found in the raw product. With the selected reaction procedure (interruption of the reaction after 12.5 Hrs), this intermediately occurring compound is fully converted to the dihydroxy compound (3R, 5S)-IV.

The integration of the four main signals in the gas chromatogram provides for the following relative intensities ((S)-VI and (S)-VII combined, retention times in brackets:

| | |
|---|---|
| (3R, 5S)-V: | 34% (8.14 mm) |
| (S)-VI/(S)-VII: | 61% (8.30/7.84 min) |
| VIII: | 5% (6.85 min) |

With the reaction procedure of the microbial reduction described herein a raw product is obtained which consists mainly of the hydroxyketone (S)-II. This result is confirmed by NMR spectroscopy (see below).

It is without doubt possible to influence the composition of the raw product by varying the reaction procedure.

The derivatisation and GC-MS analysis just described were examined with the racemic hydroxyketoester rac-II and the dia stereomer mixture of the dihydroxy compounds syn-/anti-IV, which were obtained by an independent synthesis (formula scheme III).

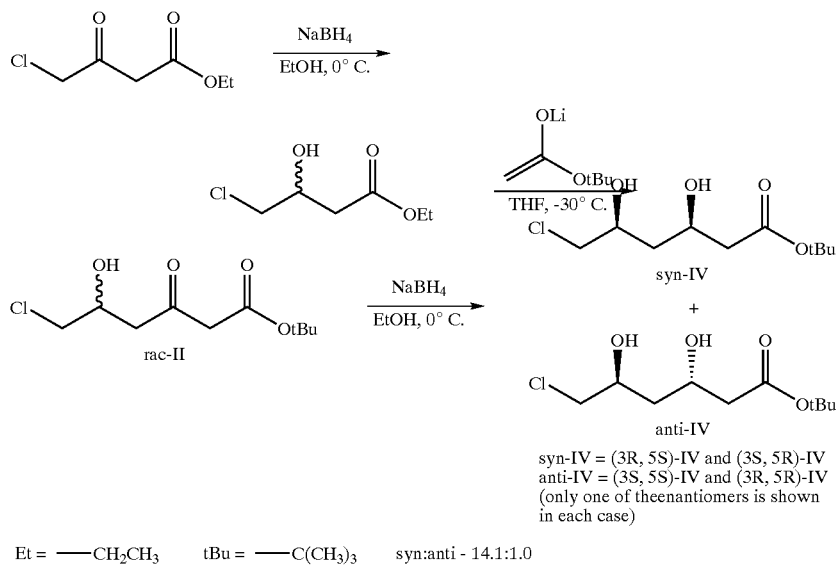

FIG. 3

The retention times and the mass spectra of these racemic samples correspond to the retention times and mass spectra of the products of the microbial reduction. The same is true for the respective TFA-derivatives (formula schematic II).

The furanone IX was also produced in an independent synthesis (formula scheme IV).

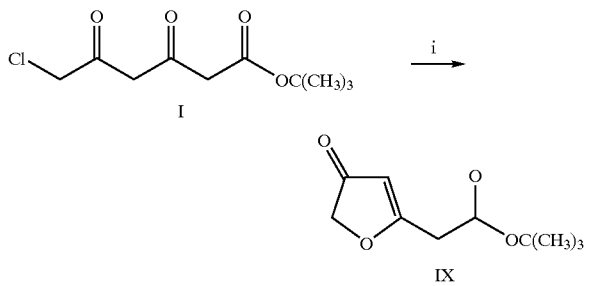

FIG. 4 i: 250 mM phosphate buffer pH 7.5/ethanol (2:1 v/v); 20 n at room temperature

Here too, the retention times and mass spectra correspond to the analogous signals in the spectra of the raw product of the microbial reduction.

b) Determination of the Diastereomer Ratio

The diastereomers syn-IV and anti-IV are not separated by the gas chromatographic method utilized. However, a baseline separation can be achieved after derivatization with TFAA/pyridine (formula scheme V).

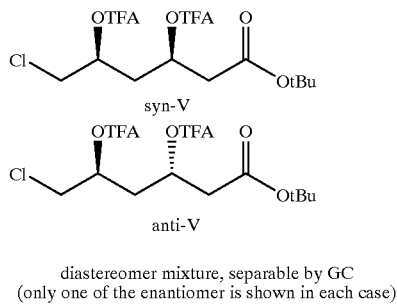

diastereomer mixture, separable by GC
(only one of the enantiomer is shown in each case)

FIG. 5

The more polar isomer anti-V has a longer retention time with respect to the syn-isomer. Both signals exhibit identical mass spectra.

Applied to the raw product of the microbial reduction, this method provides the diastereomers syn-V and anti-V at a ratio of 135:1. The microbial reduction therefore delivers the syn-isomer in a very high excess. This result is confirmed by NMR spectroscopy (See below). For the TFA derivatives of the products of the almost non-selective $NaBH_4$-reduction (formula schematic III) the integration of the GC signals results In a ratio of 1.4: 1.0.

c) NMR-Spectroscopy

The NMR spectra of the raw product of the microbial reduction confirm the results of the GC-MS analyses. The $^1$H-NMR-spectrum shows a superposition of the individual spectra of the compounds (S)-11, (3R,5S)-IV and IX, wherein the signals of the hydroxyketone (S)-II clearly dominate, whereas the signals of the furanone IX are barely visible.

Hydroxyketoester (S)-II $^1$H-NMR (300 MHz, $CDCl_3$, 22° C., only the signals of the keto form are indicated) δ: 4.31 (m, 1H, C$\underline{H}$OH), 3.6 (m, fine structure which cannot be recognized because of superposition with multiplet of compound (3R,5S)-IV; 2×H6), 3.41 (s, 2H, H2) 2.90 (dd, J=17.5, 5.0 Hz, 1H, H4) 2.83 (dd, J=17.5, 7.3 Hz 1H, H4), 1.46 (s, 3×C$\underline{H}_3$, superposition with an analogous signal of the compounds (3R, 5S)-IV and IX). Keto: Enol=about 95:5. $^{13}$C-NMR (75.5 MHz, $CDCl_3$, only the signals of the keto form are given) δ: 28.13 (OC($\underline{C}H_3$)$_3$), 46.57, 48.43, (C4, C6), 51.31 (C2), 67.58 (C5), 82.73 (O$\underline{C}$(CH$_3$)$_3$), 166.22 ($\underline{C}$OOtBu), 202.93 (C3).

Dihydroxy Compounds (3R,5S)-IV $^1$H-NMR (300 MHz, $CDCl_3$, 22° C.) δ: 4.22(m, 1H, H5), 4.05 (m, 1H, H3), 3.6 (m, the fine structure cannot be recognized because of superposition with multiplet of the compound (S)-II; 2×H6), 2.43 (d, J=6.3 Hz, 2H, H2), 1.70 (m, 3H, H4), 1.46 (s, 3×C$\underline{H}_3$, superposition with an analogous signal of the compounds (S)-II and IX). $^{13}$C-NMR (75.5 MHz, $CDCl_3$) δ: 28.27 (OC(CH$_3$)$_3$), 39.45, 42.47(C2, C4), 49.17 (C6), 68.35 (C3), 71.57 (C5), 81.90 (OC(CH$_3$)$_3$), 172.21 ($\underline{C}$OOtBu).

Furanone IX $^1$H-NMR (300 MHz, $CDCl_3$, 220° C.) δ:5.69 (s, 1H, H3), 4.54 (s, 2H, H5), 3.48 (s, 2H, H6), 1.47 (s, 3×C$\underline{H}_3$, superposition with analogous signal of the compounds (S)-II and (3R, 5S)-IV).

The shifts indicated relate to $CHCl_3$ in $CDCl_3$($^1$H-NMR: δ=7.27; $^{13}$C-NMR: δ=77.23) and they conform with the data of the comparison compounds rac-II, syn/anti-IV and IX (formula scheme III), which were independently synthesized.

The signals of the dihydroxy compound anti-IV, which differ from those of the stereoisomeric compound syn-IV cannot be observed in the $^{13}$C-NMR spectrum of the raw product of the microbial reduction. This is further proof of the very high content of the syn-isomer (see above).

Dihydroxy compound anti-IV (from an independent synthesis, see formula scheme III):

$^{13}$C-NMR (75.5 MHz, $CDCl_3$) δ: 28.27 (OC($\underline{C}H_3$)$_3$), 39.33, 42.22 (C2, C4), 49.60 (C6), 65.46(C3), 68.94(C5), 81.87(O$\underline{C}$(CH$_3$)$_3$), 172.54 ($\underline{C}$OOtBu).

The correlation of the signal sets in the $^{13}$C-NMR-spectrum of the isomer mixture syn-/anti-IV with the diastereomers occurs on the basis of the characteristic chemical displacement of the carbon atoms C-3 and C-5 (formula scheme VI).

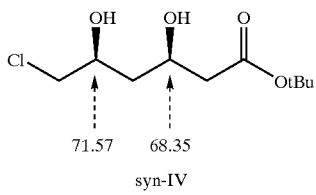

syn-IV d) F. G. Kathawala et al., Helv. Chim. Acta 1986, 69, 803–805
b) K.-M. Chen et al., Tetrahedron Lett. 1987, 28, 155–158
c) C. Bonini et al., Gazz. Chem. Ital. 1991, 121, 75–80.

The $^{13}$C-NMR-spectrum of the raw product shows accordingly that in the microbial reduction described herein the syn-isomer is formed.

d) Determination of the Absolute Configuration and the Enantiomer Purity

Since the configuration of the stereo center C-3 relative to the stereo center C-5 has been clarified already by the $^{13}$C-NMR spectroscopy the further analyzes is limited to the determination of the configuration of the stereo center C-5. To this end, the raw product of the microbial reduction is converted to the cyclic derivative (S)-X (formula scheme VII).

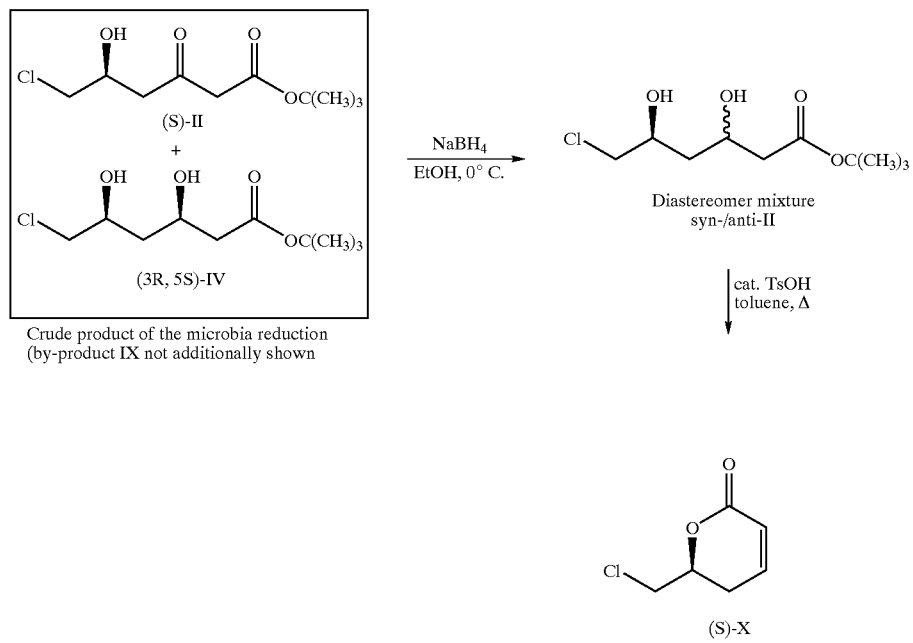

FIG. 7

TsOH = p = toluenesulfonic acid

-continued

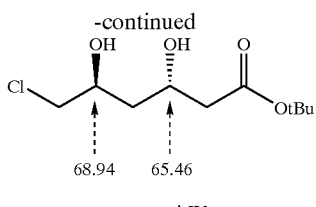

anti-IV $^{13}$C nuclear resonances in ppm
(only one of the isomers is shown in each case)

FIG. 6

In the present class of compounds (1.3-diole) the signals of the hydroxyl-carrying carbon atoms of the syn-isomer usually have a deep field shift relative to the analog signals of the anti-isomer. Compare in this respect:

The racemic derivative rac-X (formula scheme VIII), which is obtained with the same method from the hydroxyketoester rac-II can be separated by HPLC using a chiral stationary phase.

HPLC conditions: Chiracel OB (DAISO); 25° C.; 1 ml/min i hexane/i-propanol (80:20); detection at 210 nm.

Retention Times (S)-X: 24.7 min.

(R)-X: 21.5 min.

The assignment of the absolute configuration of the separated enantiomers occurs by a comparison with the retention time of an authentic sample of the lactone (S)-X, which is produced from the hydroxyketon (S)-11 (>99% ee)

in a manner corresponding to the racemic derivative rac-X (formula scheme VIII). The enantiomerically pure hydroxy ketone (S)-II is obtained in accordance with a known procedure (M. Wolberg, W. Hummel, M. Müller, pat. publ. DE 198 57 302.2, 1998).

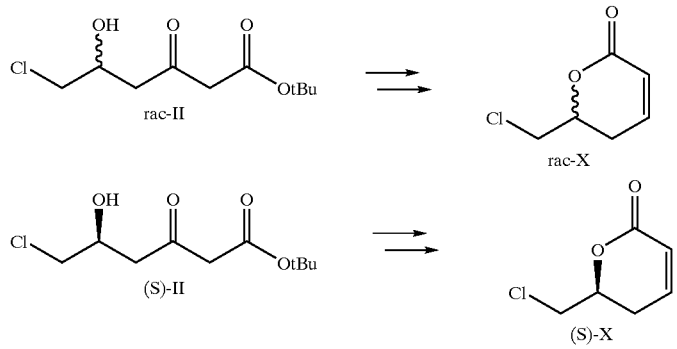

FIG. 8

> 99% ee

By integration of the signals of the derivative (S)-X, which was produced from the raw product of the microbial reduction (formula scheme VII), an enantiomeric excess of 99.4% is calculated.

What is claimed is:

1. A method of reducing diketocarboxylic acids or hydroxyketocarboxylic acids and their esters, wherein at least one keto group is converted to a hydroxyl group in the presence of lactobacillus species.

2. A method according to claim 1, wherein during the conversion of said at least one keto group to a hydroxyl group, diols are formed.

3. A method according to claim 1, wherein during the conversion of said at least one keto group to a hydroxyl group a mixture of diols, and monoalcohols is formed.

4. A method according to claim 1, wherein compounds of the formula 1:

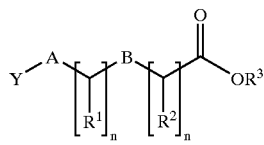

are reacted, wherein

A, B=C=O, CHOΣ, with Σ=H or a protective group for the hydroxy function, wherein A and B may be identical or different, $R^1$, $R^2$=H or a component selected from the group consisting of one of alkyl alkenyl, alkynyl, cycloalkyl, cycloalkenyl, aryl, aralkyl and cycloalkylalkyl, wherein the components may be mono- or polysubstituted by at least one of the hetero atoms Si, N, P, O, S, F, Cl, Br, and I;

$R^3$=H, metal cations or a component selected from the group consisting of alkyl, alkenyl, alkynyl, cycloalkyl, cycloalkenyl, aryl, aralkyl and cycloalkylalkyl, wherein the components may be mono- or polysubstituted by at least one of the heteroatoms Si, N, P, O, S, F, Cl, Br, and I;

Y=a component selected from the group consisting of alkyl, alkenyl, alkynyl, cycloalkyl, cycloalkenyl, aryl, aralkyl and cycloalkylalkyl, wherein the components may be mono- or polysubstituted by at least one of the heteroatoms Si, N, P, O, S, F, Cl, Br, and I;

Excluded is X-CH$_2$-O-CH$_2$—wherein * X=alkyl, aryl, cycloalkyl, arakyl or cycloakylalkyl;

n=-10.

5. A method according to claim 1, wherein compounds of the formula 2:

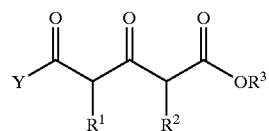

are employed, wherein $R^1$, $R^2$, $R^3$ and Y have the same meaning as in formula 1.

6. A method according to claim 1, wherein the compounds of the formula 3:

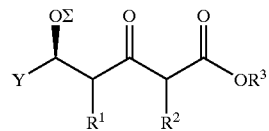

or the enantiomers thereof are employed wherein $R^1$, $R^2$, $R^3$ and Y have the same meaning as in formula 1. Σ=H or protective groups for the hydroxyl functions.

7. A method according to claim 1, wherein the compounds of the formula 4

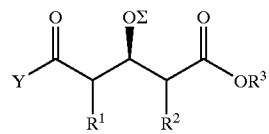

or the enantiomers thereof are utilized wherein $R^1$, $R^2$, $R^3$ and Y have the same meaning as in Formula 1. Σ=H or protective groups for the hydroxyl functions.

8. A method according to claim 1, wherein at least one of the lactobacillus kefir and the lactobacillus brevis is employed for the conversion.

9. A method according to claim 1, wherein the method is performed at a pH value of 2 to 10.

10. A method according to claim 1, wherein the method is performed at a pH value of 4 to 8.

* * * * *